United States Patent
Maeda et al.

(10) Patent No.: US 10,329,229 B2
(45) Date of Patent: Jun. 25, 2019

(54) METHOD FOR PRODUCING HIGH-CONCENTRATION ALCOHOL

(71) Applicants: MITSUBISHI CHEMICAL CORPORATION, Chiyoda-ku (JP); MITSUBISHI CHEMICAL ENGINEERING CORPORATION, Chuo-ku (JP)

(72) Inventors: Kazuhide Maeda, Tokyo (JP); Koichi Yamazaki, Mie (JP); Hiroyuki Kakiuchi, Tokyo (JP); Takeshi Tahara, Tokyo (JP); Takahiko Takewaki, Kanagawa (JP)

(73) Assignees: MITSUBISHI CHEMICAL CORPORATION, Chiyoda-ku (JP); Mitsubishi Chemical Engineering Corporation, Chuo-ku (JP)

( * ) Notice: Subject to any disclaimer, the term of this patent is extended or adjusted under 35 U.S.C. 154(b) by 0 days.

(21) Appl. No.: 15/473,732

(22) Filed: Mar. 30, 2017

(65) Prior Publication Data

US 2017/0204030 A1 Jul. 20, 2017

Related U.S. Application Data

(63) Continuation of application No. PCT/JP2015/068739, filed on Jun. 29, 2015.

(30) Foreign Application Priority Data

Oct. 30, 2014 (JP) ................................. 2014-221970

(51) Int. Cl.

| C07C 29/76 | (2006.01) |
|---|---|
| B01D 17/02 | (2006.01) |
| B01D 61/36 | (2006.01) |
| B01D 71/02 | (2006.01) |
| B01D 3/00 | (2006.01) |
| B01D 3/14 | (2006.01) |
| B01D 67/00 | (2006.01) |

(52) U.S. Cl.
CPC .............. *C07C 29/76* (2013.01); *B01D 3/005* (2013.01); *B01D 3/145* (2013.01); *B01D 17/0202* (2013.01); *B01D 61/362* (2013.01); *B01D 67/0051* (2013.01); *B01D 71/028* (2013.01); *B01D 2311/04* (2013.01); *B01D 2323/12* (2013.01)

(58) Field of Classification Search
CPC combination set(s) only.
See application file for complete search history.

(56) References Cited

U.S. PATENT DOCUMENTS

2013/0095543 A1* 4/2013 Zavrel .................... C07C 29/76
435/161

FOREIGN PATENT DOCUMENTS

| JP | 2000-334257 | 12/2000 |
| JP | 2008-86988 | 4/2008 |
| JP | 2011-16123 | 1/2011 |
| JP | 2014-118377 | 6/2014 |

OTHER PUBLICATIONS

Extended European Search Report dated Oct. 10, 2017 in Patent Application No. 15855833.8.
International Search Report dated Aug. 18, 2015 in PCT/JP2015/068739 filed on Jun. 29, 2015 (with English translation).
Written Opinion dated Aug. 18, 2015 in PCT/JP2015/068739 filed on Jun. 29, 2015.
Office Action dated Jan. 2, 2019 in European Patent Application No. 15855833.8, 5 pages.
Sato, K. et al. "Dehydrating performance of commercial LTA zeolite membranes and application to fuel grade bio-ethanol production by hybrid distillation/vapor permeation process" Microporous and Mesoporous Materials, vol. 115, No. 1, XP029237800, 2008, pp. 184-188.

\* cited by examiner

*Primary Examiner* — Ana Z Muresan
(74) *Attorney, Agent, or Firm* — Oblon, McClelland, Maier & Neustadt, L.L.P.

(57) ABSTRACT

The present invention aims at providing a method for producing a high-concentration alcohol from a water-alcohol mixture, in which the overall process is efficient and the present invention relates to a production method of a high-concentration alcohol, including a water adsorption step of adsorbing water of a water-alcohol mixture on an adsorption column to obtain a first concentrated alcohol, a water desorption step of introducing an alcohol to obtain a hydrous alcohol, and a membrane separation step of introducing the hydrous alcohol into a membrane separation unit provided with a membrane composite containing zeolite having an $SiO_2/Al_2O_3$ molar ratio of 5 to 15 to obtain a second concentrated alcohol.

10 Claims, 7 Drawing Sheets

# METHOD FOR PRODUCING HIGH-CONCENTRATION ALCOHOL

TECHNICAL FIELD

The present invention relates to a method for producing a high-concentration alcohol, particularly, a method for producing a high-concentration alcohol from a water-alcohol mixture. The present invention also relates to an apparatus for producing the high-concentration alcohol.

BACKGROUND ART

It is difficult to exclusively remove water from a mixture of an organic compound, such as alcohols, ketones and ethers, and water and purify an organic compound at high concentration only by normal rectification, since the mixture of water and an organic compound forms an azeotrope having a minimum boiling point.

Accordingly, as the method for exclusively extracting an organic compound at high concentration from a mixture of an organic compound and water, a method of removing a majority of water by distillation and thereafter, removing the remaining water by a pressure-swing adsorption apparatus (Pressure Swing Absorption; hereinafter, sometimes referred to as "PSA") using an adsorbent has been proposed (see, Patent Document 1).

In addition, as the method for dehydrating a mixture of ethanol and water without enlarging the apparatus, a method of providing a membrane separation means to intervene between a vaporizer and PSA has been proposed. Furthermore, a method of supplying a purge gas discharged from PSA to a membrane separation means and obtaining high-concentration ethanol has been proposed (Patent Document 2).

PRIOR ART LITERATURE

Patent Document

Patent Document 1: JP-A-2000-334257
Patent Document 2: JP-A-2008-86988

SUMMARY OF THE INVENTION

Problems that the Invention is to Solve

In the method disclosed in Patent Document 2, the water adsorbed on an adsorption column is desorbed by supplying ethanol as a purge gas to the adsorption column and furthermore, the purge gas from the adsorption column is supplied to a membrane separation means. The present inventors studied this method and found that since hydrous ethanol is supplied to a membrane separation means by directly compressing a purge gas from an adsorption column, the following problems emerge.

For example, since the concentration of the component desorbed changes in the course of desorption, (i) hydrous ethanol with a high water concentration may be introduced into the membrane separation means, and (ii) mechanical instability is caused in the compressor in response to fluctuation of the composition of the component desorbed. In addition, since the purge gas is compressed from a depressurized state, (iii) the compression is energetically disadvantageous in terms of the compressor power, etc., and (iv) the equipment such as pipe in the portion of depressurization step becomes too large.

The present invention has been made to solve these problems and aims at providing a method for producing a high-concentration alcohol from a water-alcohol mixture, in which the overall process is efficient.

Means for Solving the Problems

As a result of intensive studies to solve the problems above, the present inventors have found that the above-described object can be attained by using an adsorption column and a membrane separation unit in this order and furthermore, using a specific zeolite membrane composite in the membrane separation unit. The present invention has been accomplished based on this finding.

Namely, the summary of the present invention is described below.

[1] A production method of a high-concentration alcohol,
which is method for producing a high-concentration alcohol by using an adsorption column and a membrane separation unit in this order, and
in which the alcohol produced is methanol or ethanol,
which comprises:
a water adsorption step of introducing a water-alcohol mixture into the adsorption column to adsorb water on the adsorption column and obtain a first concentrated alcohol,
a water desorption step of introducing an alcohol into the adsorption column to desorb the water adsorbed and obtain a hydrous alcohol, and
a membrane separation step of introducing the hydrous alcohol into a membrane separation unit provided with a zeolite membrane composite containing zeolite having an $SiO_2/Al_2O_3$ molar ratio of 5 to 15 to obtain a second concentrated alcohol.

[2] The production method of a high-concentration alcohol according to [1], wherein the zeolite is zeolite having a framework density of 10.0 to 18.0 T/1000 Å.

[3] The production method of a high-concentration alcohol according to [1] or [2], wherein the zeolite is CHA-type zeolite.

[4] The production method of a high-concentration alcohol according to any one of [1] to [3], wherein a rectification step in a rectification column is provided before the water adsorption step and the water-alcohol mixture introduced into the adsorption column in the water adsorption step is a distillate at the top of the rectification column in the rectification step.

[5] The production method of a high-concentration alcohol according to any one of [1] to [4], wherein a plurality of adsorption columns are present.

[6] The production method of a high-concentration alcohol according to any one of [1] to [5], wherein the second concentrated alcohol obtained in the membrane separation step is reintroduced in an adsorption column in the water adsorption step.

[7] The production method of a high-concentration alcohol according to any one of [1] to [6], wherein an ethanol-containing liquid produced by alcohol fermentation with fermentative bacteria is used as a raw material.

[8] The production method of a high-concentration alcohol according to any one of [1] to [7], wherein the water-alcohol mixture contains an acid.

[9] The production method of a high-concentration alcohol according to any one of [1] to [8], wherein the membrane separation in the membrane separation step is separation by a pervaporation process.

[10] The production method of a high-concentration alcohol according to any one of [1] to [8], wherein the membrane separation in the membrane separation step is separation by a vapor permeation process.

[11] The production method of a high-concentration alcohol according to any one of [1] to [10], wherein the alcohol introduced in the water desorption step is the first concentrated alcohol obtained in the water adsorption step.

[12]
A production apparatus of a high-concentration alcohol, which is an apparatus for producing a high-concentration alcohol by using an adsorption column and a membrane separation unit in this order, and
in which the alcohol produced is methanol or ethanol,
wherein after introducing a water-alcohol mixture into the adsorption column to adsorb water on the adsorption column and obtain a first concentrated alcohol, an alcohol is introduced into the adsorption column to desorb the water adsorbed and obtain a hydrous alcohol; and
the hydrous alcohol is introduced into a membrane separation unit provided with a zeolite membrane composite containing zeolite having an $SiO_2/Al_2O_3$ molar ratio of 5 to 15 to obtain a second concentrated alcohol.

According to the present invention, a production method of a high-concentration alcohol having high purity, in which the overall process is efficient at the time of obtaining a high-concentration alcohol from a water-alcohol mixture using, as a raw material, various alcohol-containing liquids including an ethanol-containing liquid produced by alcohol fermentation with fermentative bacteria, can be provided.

MODE FOR CARRYING OUT THE INVENTION

Figure 1:
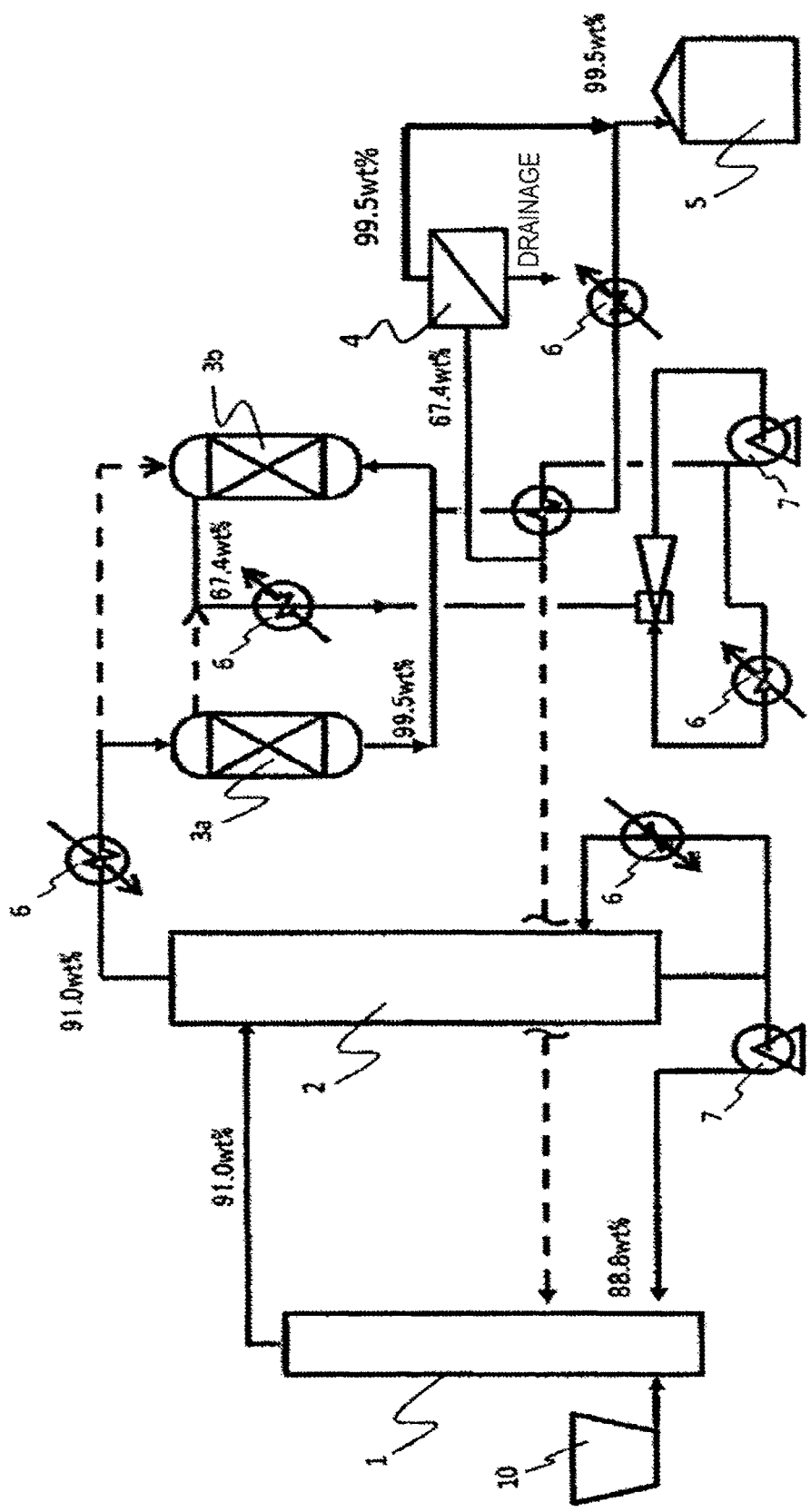
FIG. 1 is a flow diagram illustrating one example of the production method of an alcohol according to the embodiment of the present invention.

Although the present invention is described in detail below, the present invention is not limited only to specific embodiments. In the description of the present invention, "wt %" has the same meanings as "% by mass".

The present invention is a method for producing a high-concentration alcohol by using an adsorption column and a membrane separation unit in this order, in which the alcohol produced is methanol or ethanol, which includes introducing, as a water-alcohol mixture, for example, a vapor of a water-alcohol mixture into the adsorption column to adsorb water (water molecule) in the adsorption column and obtain a first concentrated alcohol; introducing an alcohol into the adsorption column to desorb the water (water molecule) adsorbed and obtain a hydrous alcohol; and introducing the hydrous alcohol into a membrane separation unit provided with a zeolite membrane composite containing zeolite having an $SiO_2/Al_2O_3$ molar ratio of 5 to 15 to obtain a second concentrated alcohol.

In addition, the present invention is an apparatus for producing a high-concentration alcohol by using an adsorption column and a membrane separation unit in this order, in which the alcohol produced is methanol or ethanol, wherein after introducing, as a water-alcohol mixture, for example, a vapor of a water-alcohol mixture into the adsorption column to adsorb water (water molecule) in the adsorption column and obtain a first concentrated alcohol, an alcohol is introduced into the adsorption column to desorb the water (water molecule) adsorbed and obtain a hydrous alcohol, and the hydrous alcohol is introduced into a membrane separation unit provided with a zeolite membrane composite containing zeolite having an $SiO_2/Al_2O_3$ molar ratio of 5 to 15 to obtain a second concentrated alcohol.

The alcohol produced in the present invention includes methanol, ethanol, or a mixture thereof.

Although the alcohol (methanol, ethanol, or a mixture thereof) applied as a raw material to the present invention is not particularly limited, it includes a crude alcohol produced by various synthesis processes, an alcohol produced by alcohol fermentation with microorganisms such as fermentative bacteria, and among others, bioethanol obtained using a biomass as a raw material.

The bioethanol is an ethanol-containing liquid produced by alcohol fermentation of a biomass raw material with microorganisms such as fermentative bacteria. The fermentative bacteria may be any as long as it is a microorganism performing alcohol fermentation by using, as a carbon source, one or more members of glucose and dimers and multimers of glucose, and the fermentative bacterium includes, for example, yeast and *Zymomonas*. The bioethanol sometimes contains an impurity such as acid, in addition to an alcohol and water.

In the present invention, a high-concentration alcohol can be produced from an ethanol mixture which does not have a high purity, such as bioethanol. In addition, a high-concentration alcohol can be produced also from an alcohol mixture that may contain an acid or other impurities, such as bioethanol.

The pH of the alcohol mixture that may contain an acid or other impurities, such as bioethanol, is usually 10 or less; 8 or less is preferable; 7 or less is more preferable, and is usually 2 or more; 3 or more is preferable; 4 or more is more preferable; and 5 or more is still more preferable. A pH in this range is associated with a tendency that the denseness of zeolite membrane is maintained and a sufficient separation performance is obtained over a long period of time.

Accordingly, the present invention is suitable as a method for producing a high-concentration alcohol by using bioethanol as a raw material and dehydrating the bioethanol.

The high-concentration alcohol as used in the present invention is an alcohol having a concentration of usually 88.0% by mass or more; 90.0% by mass or more is preferable; 95.0% by mass or more is more preferable; 98.0% by mass or more is still more preferable, 99.0% by mass or more is yet still more preferable; 99.5% by mass or more is even yet still more preferable; add 99.9% by mass or more is most preferable. In the description of the present invention, "high concentration" has the same meaning as "high purity".

The adsorption column for use in the present invention may be operated by any of pressure-swing adsorption (PSA), temperature-swing adsorption (TSA), and pressure/temperature swing adsorption (PTSA) combining both.

PSA has a function of adsorbing water etc. into an adsorbent by increasing the pressure, and desorbing water, etc. from the adsorbent by reducing the pressure. On the other hand, TSA has a function of adsorbing water, etc. into an adsorbent, and desorbing water, etc. from the adsorbent by supplying a heated gas (e.g., nitrogen) and thereby raising the temperature.

PSA, TSA and PTSA have a relatively simple apparatus configuration and are therefore widely used, and as the adsorbent, "Molecular Sieve" (trade name) that is synthetic zeolite is suitably used because of its high dehydrating ability.

Although The alcohol concentration in the water-alcohol mixture introduced into the adsorption column is not particularly limited and, for example, is usually 95% by mass or less; and 92% by mass or less is preferable, and is usually 50% by mass or more, 70% by mass or more is preferable; 80% by mass or more is more preferable; and 85% by mass or more is still more preferable. An alcohol concentration which is not more than the upper limit above is associated with a tendency that the load on, e.g., the rectification column in the previous stage is reduced and the overall energy efficiency is enhanced. An alcohol concentration which is not less than the lower limit makes it possible to avoid an excessively high water concentration, an increase in the filling amount of adsorbent, enlargement of the adsorption equipment, and a rise of the equipment cost. This tends to suppress the frequency of regenerating the adsorbent of the adsorption column and reduce the operation cost.

In the present invention, the water-alcohol mixture introduced into the adsorption column is preferably a distillate at the top of a rectification column used in a rectification step provided as a pre-step of the water adsorption step.

A distillate at the top (a mixture having an increased alcohol concentration) which is rectified in the rectification column is introduced into the adsorption column, whereby an alcohol having a higher purity can be obtained.

In the distillate at the top (mixture) rectified in the rectification column, it is preferred that the alcohol concentration is usually 70% by mass or more; 80% by mass or more is preferable; and 85% by mass or more is more preferable, and is usually 98% by mass or less; 95% by mass or less is preferable; and 90% by mass or less is more preferable. An alcohol concentration which is not more than the upper limit above is associated with a tendency that the load on, e.g., the rectification column in the previous stage is reduced and the overall energy efficiency is enhanced. An alcohol concentration not less than the lower limit makes it possible to avoid an excessively high water concentration; an increase in the filling amount of adsorbent; enlargement of the adsorption equipment; and a rise of the equipment cost. This tends to suppress the frequency of regenerating the adsorbent of the adsorption column and reduce the operation cost.

In the case where the raw material is a mixture having a low alcohol concentration, it is preferable for the mixture to be first provided to a preliminary vaporizer such as mash column and concentrated to usually 30% by mass or more; 35% by mass or more is preferable; 40% by mass or more is more preferable; and 45% by mass or more is still more preferable, and to usually less than 70% by mass; 65% by mass or less is preferable; 60% by mass or less is more preferable; and 55% by mass or less is still more preferable.

An alcohol concentration in this range makes it possible to reduce the energy consumption, because substantially no reflux is required and the amount of water to be evaporated is small.

For example, in the case of an alcohol containing many impurities, such as bioethanol, it is preferable for removing an insoluble matter or a high-molecular-weight component in the solution as necessary, to perform one kind of or a combination of a plurality of kinds of pretreatments, e.g., filtration such as microfiltration, ultrafiltration and nanofiltration, neutralization treatment, and preliminary distillation in a mash column. An ethanol mixture concentrated in the preliminary vaporizer such as mash column is then preferably provided to a rectification column.

As for the adsorption column, although it may be sufficient to use one unit, a plurality of units are preferably provided. In the case where a plurality of units are provided, a water adsorption step of removing water in the mixture is conducted at least in one adsorption column, and a water desorption step is conducted in another adsorption column. For example, when two adsorption columns are provided, in the first adsorption column, a water-alcohol mixture is introduced to adsorb water, and in the second adsorption column into which water has been already adsorbed, an alcohol is introduced to desorb the water and obtain a hydrous alcohol.

In the case of using only one adsorption column, a water adsorption step is conducted for a given time and after stopping feeding of the mixture to the adsorption column, a water desorption step is then performed.

In the water adsorption step, water in the water-alcohol mixture is adsorbed into an adsorbent, whereby the alcohol is concentrated and a high-concentration alcohol is obtained. In the present invention, the high-concentration alcohol obtained in the water adsorption step is referred to as a first concentrated alcohol.

In the water desorption step, part of the first concentrated alcohol obtained in the water adsorption step is preferably introduced into the adsorption column to desorb the adsorbed water from the adsorption column.

The alcohol concentration of the hydrous alcohol introduced into a membrane separation step is usually 40% by mass or more; 50% by mass or more is preferable; and 60% by mass or more is more preferable, and is usually 99% by mass or less; 95% by mass or less is preferable; and 90% by mass or less is more preferable.

The present invention is characterized by having a membrane separation step where the hydrous alcohol obtained in the desorption step of desorbing water from the adsorption column is introduced into a membrane separation unit and water and an alcohol of the hydrous alcohol are thereby separated.

As for the water adsorbed in the adsorption column, it is a conventional practice that the water is desorbed from the adsorption column to obtain a hydrous alcohol by introducing a high-concentration alcohol (the first concentrated alcohol of the present invention) into the adsorption column and the hydrous alcohol is then re-provided to a rectification column, etc. However, at the time of redistillation in a rectification column, a large amount of evaporation heat for evaporating a liquid is required, and this is energetically not preferred in terms of overall process. Accordingly, it would be energetically preferable if the water-alcohol mixture generated by desorption of water from the adsorption column could be separated by a membrane separation unit.

However, in an A-type zeolite separation membrane that has been conventionally widely used, when a mixture containing, for example, 20% by mass or more of water is introduced, the structure is broken. Thus, the hydrous alcohol discharged from an adsorption column cannot be directly introduced into a membrane separation unit. Accordingly, in Patent Document 2, it is made possible to desorb water from an adsorption column by supplying an alcohol as a purge gas to the adsorption column and furthermore, perform the separation in a membrane separation unit by supplying the purge gas from the adsorption column to a membrane separation means.

On the other hand, in the present invention, a zeolite membrane having a specific property is used in the membrane separation unit, so that even a mixture containing a large amount of water can be introduced into the membrane separation unit to efficiently separate water and alcohol.

Specifically, the membrane separation unit for use in the present invention has, as a separation membrane, a porous support-zeolite membrane composite (sometimes simply referred to as a zeolite membrane composite) having, on a porous support surface, a zeolite membrane containing zeolite having an $SiO_2/Al_2O_3$ molar ratio of 5 to 15. Respective components constituting the zeolite membrane composite used in this embodiment are described below.

The porous support for use in the present invention is not particularly limited as long as it has chemical stability to enable membranous fixing, preferably, crystallization, of zeolite on the surface and is porous. Among others, an inorganic porous support is preferred, and examples thereof include a ceramic sintered body such as silica, α-alumina, γ-alumina, mullite, zirconia, titania, yttria, silicon nitride and silicon carbide, a sintered metal such as iron, bronze and stainless steel, glass, and a carbon molding.

Among inorganic porous supports, a porous support containing a material (ceramic support) obtained by sintering a ceramic that is a solid material in which the basic component or a majority thereof is composed of an inorganic nonmetallic substance, has an effect of enhancing the interfacial adherence by being zeolitized in part during the synthesis of a zeolite membrane and is therefore preferred.

Specifically, the porous support includes a ceramic sintered body (ceramic support) such as silica, α-alumina, γ-alumina, mullite, zirconia, titania, yttria, silicon nitride, silicon carbide, etc. Among these, a porous support containing at least one of alumina, silica and mullite is more preferred in that partial zeolitization of the porous support is facilitated and binding between porous support and zeolite, particularly CHA-type zeolite, is therefore strengthened, as a result, a dense membrane having high separation performance is more readily formed.

By virtue of having a support, the zeolite membrane composite is provided with increased mechanical strength and easy handling; and making various device designs possible. In the case of an inorganic porous support, the support is composed of an inorganic material and therefore, is excellent in heat resistance and chemical resistance.

The shape of the porous support for use in the present invention is not limited as long as a liquid or gas mixture can be effectively separated, and specifically, the shape includes a plate, a tube, a cylinder, a honeycomb in which many columnar or prismatic holes are present, a monolith, etc. The porous support may have any of these shapes.

In the porous support for use in the present invention, zeolite is preferably crystallized on its surface (hereinafter, sometimes referred to as "porous support surface").

Although the average pore size of the porous support surface is not particularly limited, it is preferably controlled. It is preferred that the pore size is usually 0.02 μm or more; 0.05 μm or more is preferable; 0.1 μm or more is more preferable; and 0.5 μm or more is still more preferable, and is usually 20 μm or less; 10 μm or less is preferable; and 5 μm or less is more preferable.

If the average pore size is too small, the permeation amount tends to decrease, whereas if it is too large, the strength of the support itself may be insufficient, or the proportion of pores on the support surface is increased, making it difficult to form a dense zeolite membrane.

The average thickness (wall thickness) of the porous support is usually 0.1 mm or more; 0.3 mm or more is preferable; 0.5 mm or more is more preferable; and 0.7 mm or more is still more preferable, and is usually 7 mm or less; 5 mm or less is preferable; and 3 mm or less is more preferable.

Although the support is used with the purpose of imparting mechanical strength to the zeolite membrane, if the average thickness of the support is too small, it is likely that the porous support-zeolite membrane composite does not have sufficient strength and the porous support-zeolite membrane composite is weak against impact, vibration, etc. to cause a problem in practice. If the average thickness of the support is too large, the permeated substance tends to poorly diffuse, resulting in a low permeation flux.

In the case where the porous support is a cylindrical tube, the outer diameter of the cylindrical tube is usually 3 mm or more; 5.5 mm or more is preferable; 9.5 mm or more is more preferable; 11 mm or more is still more preferable, and is usually 51 mm or less, 31 mm or less is preferable; 21 mm or less is more preferable; 17 mm or less is still more preferable, and 15 mm or less is yet still more preferable.

Although the support is used with the purpose of imparting mechanical strength to the zeolite membrane, in the case where the support is a cylindrical tube, if the outer diameter thereof is too small, it is likely that the porous support-zeolite membrane composite does not have sufficient strength and the porous support-zeolite membrane composite is weak against impact, vibration, etc. to cause a problem in practice. In the case where the support is a cylindrical tube, if the outer diameter thereof is too large, the membrane area per volume tends to decrease, the membrane volume needed becomes large for obtaining the membrane needed, as result, the wide installation location is needed and large module is needed, thereby leading to economical disadvantage.

The surface of the porous support is preferably smooth and, if desired, the surface may be polished with a file, etc.

Here, the porous support surface means, for example, an inorganic porous support surface portion on which zeolite is crystallized, and as long as it is a surface, the surface may be any surface of each shape or may be a plurality of faces. For example, in the case of a cylindrical tube support, the surface may be the outer-side surface or the inner-side surface and depending on the case, may be both outer-side and inner-side surfaces.

In the porous support for use in the present invention, the pore size of the portion other than the porous support surface is not limited.

The porosity of the porous support is usually 20% or more; 25% or more is preferable; and 30% or more is more preferable, and is usually 70% or less; 60% or less is preferable; and 50% or less is more preferable.

The porosity of the porous support governs the permeation flow rate at the time of separation of a gas or a liquid, and if it is less than the lower limit above, diffusion of the permeated material tends to be inhibited, whereas if the porosity exceeds the upper limit above, the strength of the porous support is likely to decrease.

The zeolite having an $SiO_2/Al_2O_3$ molar ratio of 5 to 15 is described below.

The $SiO_2/Al_2O_3$ molar ratio is usually 5 or more; 5.5 or more is preferable; 6 or more is more preferable; and 7 or more is still more preferable, and is usually 15 or less; 14 or less is preferable; 12 or less is more preferable; 10 or less is still more preferable; 9 or less is yet still more preferable; and 8 or less is even yet still more preferable. When the $SiO_2/Al_2O_3$ molar ratio is in this range, the zeolite membrane becomes a membrane excellent in hydrophilicity and also excellent in acid resistance and water resistance and is suitably used also for the separation of a substance reacting with an acid site. In particular, an $SiO_2/Al_2O_3$ molar ratio in this range is suitable for the separation of methanol and ethanol each having a large water content. The $SiO_2/Al_2O_3$ molar ratio can be adjusted by the reaction conditions of the later-described hydrothermal synthesis.

Here, the $SiO_2/Al_2O_3$ molar ratio is a numerical value obtained by measuring the zeolite side of a zeolite membrane composite by scanning electron microscope-energy dispersive X-ray spectroscopy (SEM-EDX). The measurement is usually performed at an X-ray accelerating voltage of 10 kV so as to obtain information of only a membrane having a thickness of several μm.

In the present invention, although the framework density of the main zeolite constituting the zeolite membrane is not particularly limited, it is preferably 10.0 T/1000 Å or more; and 12.0 T/1000 Å or more is more preferable, and is preferably 18.0 T/1000 Å or less; 17.0 T/1000 Å or less is more preferable; 16.0 T/1000 Å or less is still more preferable; and 15.0 T/1000 Å or less is most preferable. The framework density preferably falls in this range in view of durability.

The framework density means the number of T elements except for oxygen, constituting the framework per 1,000 Å$^3$ of zeolite, and this value depends on the zeolite structure. Incidentally, the relationship between the framework density and the zeolite structure is described in ATLAS OF ZEOLITE FRAMEWORK TYPES, Fifth Revised Edition, 2001, ELSEVIER.

The main zeolite constituting the zeolite membrane in the present invention usually includes zeolite having an oxygen 6- to 10-membered ring structure; and zeolite having an oxygen 6- to 8-membered ring structure is preferable.

The value of n of the zeolite having an oxygen n-membered ring, as used herein, indicates a pore having a largest number of oxygen atoms among pores composed of oxygen and T elements forming the zeolite framework. For example, in the case where pores of oxygen 12-membered and 8-membered rings are present as in MOR-type zeolite, the zeolite is regarded as oxygen 12-membered ring zeolite.

The zeolite having an oxygen 6- to 10-membered ring structure includes, for example, AEI, AEL, AFG ANA, BRE, CAS, CDO, CHA, DAC, DDR, DOH, EAB, EPI, ESV, EUO, FAR, FRA, FER, GIS, GIU, GOO, HEU, IMF, ITE, ITH, KFI, LEV, LIO, LOS, LTN, MAR, MEP, MER, MEL, MFI, MFS, MON, MSO, MTF, MTN, MTT, MWW, NAT, NES, NON, PAU, PHI, RHO, RRO, RTE, RTH, RUT, SGT, SOD, STF, STI, STT, TER, TOL, TON, TSC, TUN, UFI, VNI, VSV, WEI, and YUG The preferable zeolite having an oxygen 6- to 8-membered ring structure includes, for example, AEI, AFG, ANA, CHA, EAB, ERI, ESV, FAR, FRA, GIS, ITE, KFI, LEV, LIO, LOS, LTN, MAR, PAU, RHO, RTH, SOD, STI, TOL, and UFI.

The oxygen n-membered ring structure determines the pore size of zeolite, and in the zeolite having pores smaller than 6-membered ring, the pore diameter is smaller than the Kinetic radius of an $H_2O$ molecule, as a result, the permeation flux is reduced and not practicable. In the case of larger than oxygen 10-membered ring structure, the pore size becomes large, and the separation performance for a small-size organic material may be reduced, resulting in limited application.

Among the zeolite structures above, those having the above-described $SiO_2/Al_2O_3$ molar ratio are preferred; AEI, CHA, KFI, LEV, PAU, RHO, RTH, and UFI are more preferred; CHA, LEV, and UFI are still more preferred; and CHA is most preferred. The zeolite is preferably an aluminosilicate.

The CHA-type zeolite is described below. The CHA-type zeolite suitably used in the present invention indicates zeolite having a CHA structure in terms of the code assigned to the zeolite structure by International Zeolite Association (IZA). This is zeolite having the same crystal structure as that of the naturally-occurring chabazite. The CHA-type zeolite takes on a structure characterized by having a three-dimensional pore composed of an oxygen eight-membered ring with a size of 3.8×3.8 Å, and the structure is defined by X-ray diffraction data.

The framework density of the CHA-type zeolite used in the present invention is 14.5 T/1,000 Å.

As the component constituting the membrane, for example, an inorganic binder such as silica and alumina, an organic material such as polymer, and a silylating agent for modifying the zeolite surface, may be contained, if desired, in addition to zeolite.

Although the zeolite membrane in the present invention may partially contain an amorphous component, etc., a zeolite membrane composed of substantially only zeolite is preferable; a zeolite membrane containing CHA-type zeolite as a main component, which may partially contain zeolite of other structures such as mordenite or MFI or may contain an amorphous component, etc., is more preferable, and a zeolite membrane composed of substantially only CHA-type zeolite is still more preferable.

In the membrane separation step, the zeolite membrane containing zeolite having an $SiO_2/Al_2O_3$ molar ratio of 5 to 15 and another separation membrane may be used in combination.

For example, after separating a hydrous alcohol by using the zeolite membrane composite containing zeolite having an $SiO_2/Al_2O_3$ molar ratio of 5 to 15, the permeated liquid may be separated by another separation membrane. In addition, after separating a hydrous alcohol by another separation membrane, the permeated liquid may be separated using the zeolite membrane composite containing zeolite having an $SiO_2/Al_2O_3$ molar ratio of 5 to 15.

As another separation membrane, the zeolite membrane may be combined specifically with an LTA-type zeolite membrane, an FAU-type zeolite membrane, or a zeolite membrane with the $SiO_2/Al_2O_3$ molar ratio exceeding 15. For example, the zeolite membrane may be combined with a CHA-type zeolite membrane in which the $SiO_2/Al_2O_3$ molar ratio exceeds 15.

For example, after separating a hydrous alcohol by using the zeolite membrane containing zeolite having an $SiO_2/Al_2O_3$ molar ratio of 5 to 15, the concentrated alcohol component obtained may be further dehydrated using an LTA-type zeolite membrane. Such a combination of a plurality of kinds of zeolite membranes may make it possible to enhance the process efficiency or make the apparatus compact and thereby obtain an economical advantage. The alcohol concentration of the concentrated alcohol component introduced into the LTA-type zeolite membrane is usually 80% by mass or more; 85% by mass or more is preferable; 90% by mass or more is more preferable; and 95% by mass or more is still more preferable, and is usually 99.5% by mass or less; 99.0% by mass or less is preferable; and 98.0% by mass or less is more preferable. When the concentrated alcohol component has a concentration in this range, a stable performance can be achieved for a long period of time without breaking the LTA-type zeolite membrane. In addition, the economical advantage of combining a zeolite membrane containing zeolite having an $SiO_2/Al_2O_3$ molar ratio of 5 to 15 and an LTA-type zeolite membrane increases.

Although the thickness of the zeolite membrane used in the present invention is not particularly limited, it is usually 0.1 µm or more; 0.6 µm or more is preferable; 1.0 µm or more is more preferable; 5 µm or more is still more preferable; and 7 µm or more is yet still more preferable, and is usually 100 µm or less; 60 µm or less is preferable; and 20 µm or less is more preferable. If the membrane thickness is too large, the permeation amount tends to decrease, whereas if it is too small, the selectivity or membrane strength is likely to deteriorate.

Although the particle diameter of the zeolite forming the zeolite membrane used in the present invention is not particularly limited, if it is too small, for example, a large grain boundary tends to be generated, leading to deterioration of the permeation selectivity, etc. Accordingly, the particle diameter is usually 30 nm or more, preferably 50 nm or more, more preferably 100 nm or more, and the upper limit is not more than the thickness of the membrane. It is more preferable for the particle diameter of zeolite to be the same as the thickness of the membrane, because when the particle diameter of zeolite is the same as the thickness of the membrane, the grain boundary size of zeolite becomes smallest. A zeolite membrane obtained by hydrothermal synthesis is preferred, because the particle diameter of zeolite and the thickness of the membrane sometimes becomes the same.

In the present invention, the zeolite membrane composite is a membrane formed by membranous fixing of zeolite on a porous support surface and is preferably in a state where part of zeolite is fixed even inside the porous support.

The method for forming such a zeolite membrane composite includes, for example, a method of forming the composite by membranous crystallization of zeolite on a porous support, a method of fixing zeolite on a porous support by using an inorganic binder, an organic binder, etc., a method of fixing a polymer having dispersed therein zeolite, and a method of impregnating a porous support with a zeolite slurry and depending on the case, fixing zeolite on the porous support by suction.

It is preferable that the zeolite membrane composite for use in the present invention is a membrane formed by membranous crystallization of zeolite on a porous support surface. Specifically, a membrane composite produced by a method of forming, on a porous support, a zeolite membrane having CHA-type zeolite by hydrothermal synthesis using an aqueous reaction mixture containing an Si element source, an Al element source and water is preferred, and a membrane composite formed by membranous crystallization of CHA-type zeolite on a porous support by hydrothermal synthesis is more preferred.

It is preferable that the zeolite membrane for use in the present invention is a membrane having no acid site at the time of separation of alcohol, and therefore, a membrane formed on a porous support by hydrothermal synthesis using an aqueous reaction mixture which does not contain an organic material such as organic template, from which an acid site can be derived, is preferred.

The organic template as used herein indicates a material that is an organic compound out of structure-directing agents having a function of regulating the crystal structure of the produced zeolite, i.e., a function as a template.

The hydrothermal synthesis may be performed, for example, in such a manner that a reaction mixture for hydrothermal synthesis homogenized by adjusting the composition (hereinafter, the mixture is sometimes referred to as "aqueous reaction mixture") is put in a heat-resistant pressure-resistant vessel such as autoclave, a porous support is loosely fixed in the inside of the heat-resistant pressure-resistant vessel, and the vessel is tightly closed and heated for a given time.

It is preferable that the aqueous reaction mixture is a mixture containing an Si element source, an Al element source and water and, if desired, further containing an alkali source.

As the Si element source used in the aqueous reaction mixture, for example, amorphous silica, colloidal silica, silica gel, sodium silicate, amorphous aluminosilicate gel, tetraethoxysilane (TEOS), and trimethylethoxysilane may be used.

As the Al element source, for example, sodium aluminate, aluminum hydroxide, aluminum sulfate, aluminum nitrate, aluminum oxide, and amorphous aluminosilicate gel may be used. In addition to the Al element source, the mixture may contain other element sources, for example, an element source such as Ga, Fe, B, Ti, Zr, Sn and Zn.

As the alkali source, for example, a hydroxide ion, an alkali metal hydroxide such as NaOH and KOH, and an alkaline earth metal hydroxide such as $Ca(OH)_2$, may be used. Although the kind of the alkali is not particularly limited, the alkali is usually Na, K, Li, Rb, Cs, Ca, Mg, Sr or Ba; Na or K is preferable; and K is more preferable. Two or more kinds of alkalis may be used in combination and, specifically, it is preferable to use Na and K in combination.

The ratio between the Si element source and the Al element source in the reaction mixture is usually expressed as the molar ratio of oxides of respective elements, i.e., the $SiO_2/Al_2O_3$ molar ratio (hereinafter, sometimes simply referred to as "$SiO_2/Al_2O_3$ ratio"). The $SiO_2/Al_2O_3$ ratio is 5 or more; 6 or more is preferable; 7 or more is more preferable; 7.5 or more is still more preferable; and 8 or more is yet still more preferable, and is preferably 14 or less; 12 or less is more preferable; and 10 or less is still more preferable.

When the $SiO_2/Al_2O_3$ molar ratio is in this range, the zeolite membrane is densely produced and furthermore, the produced zeolite exhibits strong hydrophilicity to allow for selective permeation of a hydrophilic compound, among others, water, from an organic compound-containing mixture. In addition, a zeolite membrane being highly acid-resistant and insusceptible to dealuminization is obtained.

The ratio between the Si element source and the alkali source is, in terms of $M_{(2/n)}O/SiO_2$ (wherein M represents an alkali metal or an alkaline earth metal, and n represents its valence of 1 or 2) molar ratio, usually 0.05 or more; 0.1 or more is preferable; and 0.2 or more is more preferable, and is usually 1.0 or less; 0.7 or less is preferable; and 0.5 or less is more preferable.

The ratio between the Si element source and water is, in terms of molar ratio of water to $SiO_2$ ($H_2O/SiO_2$ molar ratio), usually 10 or more; 30 or more is preferable; 40 or more is more preferable; 50 or more is still more preferable; 60 or more is yet still more preferable; and 70 or more is most preferable, and is usually 1,000 or less; 500 or less is preferable; 200 or less is more preferable; and 100 or less is still more preferable.

When the molar ratios of the substances in the aqueous reaction mixture are in the ranges above, a denser zeolite membrane can be produced. The amount of water is particularly important in producing a dense zeolite membrane, and it is likely that under the conditions where the amount of water is large relative to silica, production of spontaneous nuclei in a liquid is decreased and crystal growth from a seed crystal on a support is promoted to facilitate formation of a dense membrane, in comparison with general conditions of the powder synthesis method.

In general, the amount of water at the time of synthesis of a powdery zeolite is approximately from 15 to 50 in terms of $H_2O/SiO_2$ molar ratio. By setting the $H_2O/SiO_2$ molar ratio to be high (from 50 to 1000), i.e., creating a condition where the amount of water is large, a porous support-zeolite membrane composite containing zeolite crystallized as a dense membrane on a support and having high separation performance can be obtained.

In particular, it is preferable that the zeolite membrane having the characteristics of the present invention is a CHA-type zeolite membrane formed by using FAU-type zeolite as the seed crystal and performing hydrothermal synthesis in the presence of the seed crystal.

The FAU-type zeolite used as the seed crystal may be any zeolite as long as its structure is of FAU-type, and the FAU-type zeolite includes, for example, a silicate and a phosphate. The silicate includes, for example, an aluminosilicate, a gallosilicate, a ferrisilicate, a titanosilicate, and a borosilicate, and the phosphate includes an aluminophosphate composed of aluminum and phosphorus (called ALPO, such as ALPO-5), a silicoaluminoposphate (called SAPO, such as SAPO-34) composed of silicon, aluminum and phosphorus, and a metalloaluminosilicate called MeAPO, such as FAPO-5 containing Fe or other elements. Among these, an aluminosilicate and a silicoalumiophosphate are preferred, and an aluminosilicate is more preferred.

Although the FAU-type zeolite generally includes X-type zeolite and Y-type zeolite, and either one or a mixture thereof may be used, it is preferable to use Y-type zeolite.

As the FAU-type zeolite used as the seed crystal, a commercially available X-type zeolite or Y-type zeolite may be used, or the zeolite may be synthesized. A general synthesis method is described, for example, VERIFIED SYNTHESES OF ZEOLITIC MATERIALS, Second Revised Edition, 2001, ELSEVIER, p. 157.

In addition, the FAU-type zeolite used may be proton-type zeolite, zeolite that is ion-exchanged with an alkali metal ion, an alkaline earth metal ion or a transition metal ion, or a mixture thereof. The alkali metal ion includes $Na^+$, $K^+$, $Li^+$, etc., the alkaline earth metal ion includes $Ca^{2+}$, $Mg^{2+}$, $Sr^{2+}$, $Ba^{2+}$, etc., and the transition metal ion includes Fe, Cu, Zn, etc. Among these, an alkali metal ion such as $Na^+$, $K^+$ and $Li^+$ is preferred.

The ion exchange may be performed, for example, by a method where FAU-type zeolite is treated with aqueous solution containing a nitrate such as $NH_4NO_3$ and $NaNO_3$, a hydroxide salt such as NaOH, an acetate such as $CH_3COONa$, or an exchanging ion, and depending on the case, with an acid such as hydrochloric acid, and then water-washed.

The concentration of the aqueous solution is usually 0.00001 mol/L or more; 0.0001 mol/L or more is preferable; and 0.001 mol/L or more is more preferable, and is usually 10 mol/L or less; 5 mol/L or less is preferable; and 2 mol/L or less is more preferable.

The temperature at the time of treatment is usually 10° C. or more; 30° C. or more is preferable; and 50° C. or more is more preferable, and is usually 200° C. or less; 150° C. or less is preferable; and 130° C. or less is more preferable.

The treating time is usually 2 hours or more; 5 hours or more is preferable; 10 hours or more is more preferable; and 20 hours or more is still more preferable, and is usually 10 days or less; 7 days or less is preferable; and 4 days or less is more preferable. Furthermore, the zeolite may be calcined at 200 to 500° C., if desired.

It is preferable to finally become a proton type, an Na type, a K type, or a mixture thereof; an Na type, a proton time, or a mixture thereof is more preferable.

The $SiO_2/Al_2O_3$ ratio as measured by the ICP emission spectral analysis of the seed crystal is usually less than 15; less than 12 is preferable; and less than 10 is more preferable, and is usually 1 or more; and 3 or more is preferable.

Although the grain size of the seed crystal is not particularly specified, it is preferred that at least one maximum value of the particle diameter obtained by the particle size distribution measurement falls in a specific size range.

Here, the maximum value indicates a maximum value of a particle size distribution graph (a graph representing the particle diameter as the abscissa and representing the relative particle amount on a volume basis as the ordinate) obtained by the particle size distribution measurement. It is preferable that the maximum value is 5 µm or less; 3 µm or less is more preferable; 2 µm or less is still more preferable; and 1.8 µm or less is yet still more preferable, and is usually 0.1 µm or more; 0.5 µm or more is preferable; and 0.8 µm or more is more preferable.

When the particle diameter is not more than the upper limit above, the seed crystal is successfully supported on a base material, and a zeolite membrane with little defects is readily formed, whereas when the particle diameter is not less than the lower limit above, the seed crystal is less likely to be melted during synthesis, and a zeolite membrane with little defects is readily formed.

Although the particle diameter distribution of the seed crystal is not particularly limited, it is preferred that the diameter D50 giving a height of 50% in the cumulative distribution diagram (on a volume basis, accumulated from the smallest particle diameter) obtained by the particle size distribution measurement is usually 0.5 gun or more; and 1.0 µm or more is preferable, and is preferably 5.0 µm or less; 4.0 µm or less is more preferable, 3.0 µm or less is still more preferable.

The proportion of the seed crystal present in the range between 0.5 times and 20 times of the average pore size of the support is usually 5% or more; 15% or more is preferable; and 25% or more is more preferable, and is usually 100%/or less; 90% or less is preferable; and 80% or less is more preferably. Within this range, the seed crystal is successfully supported on a base material, and a dense and high-performance zeolite membrane can be synthesized.

The grain size of the seed crystal is controlled in this way, whereby the condition of the seed crystal supported on the base material can be controlled and a dense membrane with little defects is formed.

In order to adjust the seed crystal to a preferable size, the crystal of commercially available FAU-type zeolite, synthetically-obtained FAU-type zeolite, or ion-exchanged FAU-type zeolite may be pulverized by means of a ball mill, a jet mill, etc.

As the method for adding a seed crystal, for example, a method of allowing a seed crystal to have been attached onto the support is preferably used. By previously attaching a seed crystal onto the support, a dense zeolite membrane having good separation performance is likely to be produced.

The method for attaching a seed crystal onto a support is not particularly limited and, for example, a dip method of dispersing the seed crystal in a solvent such as water and dipping the support in the dispersion liquid, thereby attaching the seed crystal, and a method of mixing the seed crystal with a solvent such as water to make a slurry and applying the slurry on the support, may be used. For controlling the amount of the seed crystal attached and producing a zeolite membrane composite with good reproducibility, a dip method is preferred.

Although the dispersion medium in which the seed crystal is dispersed is not particularly limited, among others, water is preferred. If desired, the pH of the dispersion liquid may be adjusted by adding hydrochloric acid or a water-soluble substance such as sodium hydroxide and potassium hydroxide. In the case of adjusting the pH, it is preferable to adjust the pH of the dispersion liquid to usually 7.5 or more; 8 or more is preferable; 10 or more is more preferable, and usually 14 or less; and 12 or less is preferable. By adjusting the pH of the dispersion liquid to this range, the amount of the seed crystal attached is easily controlled to fall in the preferable range.

The amount of the seed crystal dispersed is not particularly limited and is, relative to the total mass of the dispersion liquid, usually 0.01% by mass or more; 0.1% by mass or more is preferable; and 0.5% by mass or more is more preferable, and usually 20% by mass or less; 10% by mass or less is preferable; 5% by mass or less is more preferable; 4% by mass or less is still more preferable; and 3% by mass or less is yet still more preferable.

If the amount of the seed crystal dispersed is too small, since the amount of the seed crystal attached onto the support is small, a portion in which zeolite is not produced may be partially created on the support at the time of hydrothermal synthesis to provide a defective membrane. The amount of the seed crystal attached onto the support by a dip method becomes substantially constant when the amount of the seed crystal in the dispersion liquid reaches above a certain level. Therefore, an excessively large amount of the seed crystal in the dispersion liquid wastes a lot of seed crystal and is disadvantageous in view of the cost.

The amount of the seed crystal that has been previously attached onto the support is not particularly limited and is, in terms of the mass per 1 m$^2$ of the base material, usually 0.01 g or more; and 0.1 g or more is preferable, and usually 100 g or less; 50 g or less is preferable; 10 g or less is more preferable; 5 g or less is still more preferable; 3 g or less is yet still more preferable; and 1 g or less is most preferable.

When the amount of the seed crystal is not less than the lower limit, a crystal is readily formed, providing successful membrane growth and uniform membrane growth. When the amount of the seed crystal is not more than the upper limit, the unevenness of the surface is less likely to be increased by the seed crystal, and crystal growth from a seed crystal fallen from the support is reduced, as a result, the membrane growth on the support is hardly inhibited. Accordingly, within this range, a dense zeolite membrane tends to be readily produced.

In the case of forming the zeolite membrane on the support by hydrothermal synthesis, the method for fixing the support is not particularly limited, and the support may be fixed in any of vertical, horizontal and other configurations. In this case, the zeolite membrane may be formed by a static method, or the zeolite membrane may be formed by stirring the aqueous reaction mixture.

Although the temperature at the time of forming the zeolite membrane is not particularly limited, it is usually 80° C. or more; 100° C. or more is preferable; and 140° C. or more is more preferable, and is usually 200° C. or less; and 190° C. or less is preferable. If the reaction temperature is too low, zeolite may not be produced. If the reaction temperature is too high, zeolite of a type different from the zeolite in the present invention may be produced.

Although the heating time is not particularly limited, it is usually 1 hour or more, preferably 5 hours or more, more preferably 10 hours or more, and is usually 10 days or less, preferably 5 days or less, more preferably 3 days or less, still more preferably 2 days or less. If the reaction time is too short, zeolite may not be crystallized. If the reaction time is too long, zeolite of a type different from the zeolite in the present invention may be produced.

The pressure at the time of formation of the zeolite membrane is not particularly limited, and a self-generated pressure which is created when the aqueous reaction mixture is heated in a closed vessel at the temperature in the range above may be sufficient. If desired, an inert gas such as nitrogen may be added.

The porous support-zeolite membrane composite obtained by hydrothermal synthesis is washed with water, then subjected to a heat treatment and thereby dried. The heat treatment as used herein means to dry the porous support-zeolite membrane composite by applying heat.

In the case of aiming at drying, the temperature of the heat treatment is usually 50° C. or more; 80° C. or more is preferable; and 100° C. or more is more preferable, and is usually 200° C. or less; and 150° C. or less is preferable.

In the case of aiming at drying, the heating time is not particularly limited as long as the time is long enough to sufficiently dry the zeolite membrane, and it is preferable that the heating time is 0.5 hours or more; and 1 hour or more is more preferable. The upper limit is not particularly limited and is usually within 100 hours; within 10 hours is preferable; and within 5 hours is more preferable.

In the case of aiming at calcination of the organic template, the temperature of the heat treatment is usually 350° C. or more; 400° C. or more is preferable; 430° C. or more is more preferable; and 480° C. or more is still more preferable, and is usually 900° C. or less; 850° C. or less is preferable; 800° C. or less is more preferable; and 750° C. or less is still more preferable.

In the case of aiming at calcination of the organic template, the heating time is not particularly limited as long as the time is long enough to calcine the organic template, and it is preferable that the heating time is 0.5 hours or more; and 1 hour or more is more preferable. The upper limit is not particularly limited and is usually within 200 hours; within 100 hours is preferable; within 50 hours is more preferable; and within 20 hours is still more preferable.

The zeolite membrane may be ion-exchanged, if desired. The ion as the exchanging ion includes, for example, a proton, an alkali metal ion such as $Na^+$, $K^+$ and $Li^+$, an alkaline earth metal ion such as $Ca^{2+}$, $Mg^{2+}$, $Sr^{2+}$ and $Ba^{2+}$, and an ion of a transition metal such as Fe, Cu and Zn. Among these, an alkali metal ion such as $Na^+$, $K^+$ and $Li^+$ is preferred.

The ion exchange may be performed, for example, by a method where the zeolite membrane after the heat treatment is treated with an aqueous solution containing a nitrate such as $NH_4NO_3$ and $NaNO_3$ or an exchanging ion, usually at a temperature of from room temperature to 100° C. and then washed with water.

The zeolite membrane may be, if desired, subjected to a silylation treatment using a silylating agent. The silylating agent used for the silylation treatment includes, for example, an alkoxysilane such as tetramethoxysilane, tetraethoxysilane, tetraproxysilane, tetraisoproxysilane and tetrabutoxysilane, and a silicate oligomer such as methyl silicate oligomer and ethyl silicate oligomer. Among these, tetraethoxysilane and methyl silicate oligomer are preferred.

The silylation treatment includes, for example, a method where the zeolite membrane after the heat treatment is dipped in a silylating agent-containing solution and then heat-treated at a temperature of from room temperature to usually 150° C.; and to preferably 100° C., to obtain the membrane by washing with water, and a method where the zeolite membrane after the heat treatment is coated with a silylating agent and then heat-treated in the co-presence of water vapor at a temperature of usually from room temperature to 150° C. to obtain the membrane.

Although the zeolite membrane for use in the present invention is not particularly limited in its position on the porous support surface, in the case of using a tubular porous support, the zeolite membrane may be formed on the outer surface or inner surface and depending on the system to which applied, may be formed on both surfaces. In addition, the zeolite membrane may be stacked on a surface of the porous support or may be crystallized to fill the inside of a pore in the porous support surface. In this case, it is important that a crack or a continuous micropore is not present inside the crystallized membrane layer, and forming a so-called dense membrane leads to enhancement of the separation performance.

Although in the separation step using the membrane separation unit according to the present invention, a pervaporation (PV) process or a pervaporation permeation (VP) process is employed, in the present invention, in view of energy efficiency, it is more preferable to employ a pervaporation (PV) process.

In the PV method, a hydrous alcohol liquid is put into contact with the separation membrane to allow permeation of water. More specifically, this system is also called a permeation-vaporization method or a penetration-vaporization method and is a method where a mixture (provided liquid) is evaporated through the separation membrane and at this time, only water is allowed to permeate, whereby alcohol is separated and concentrated. Since the provided liquid is cooled by vaporization heat, a heating device to compensate the cooling is required.

The alcohol obtained after introduction into the membrane separation unit according to the present invention, when its concentration is sufficiently high, may be directly used as a product (manufactured product) or when the concentration is not sufficiently high, may be re-introduced into the adsorption column.

In the present invention, the high-concentration alcohol obtained after introduction into the membrane separation unit is referred to as a second concentrated alcohol.

In the present invention, the first concentrated alcohol and the second concentrated alcohol are preferably combined to obtain a product, i.e., a high-concentration alcohol. The first concentrated alcohol and the second concentrated alcohol may be sufficient if each is in the concentration range defined above of the high-concentration alcohol, and it is not necessarily required for both to have the same concentration.

It is preferable that the permeation of flux of water in the membrane separation step using the membrane separation unit is 0.1 kg/(m²·h) or more; 2.0 kg/(m²·h) or more is more preferable; and 5.0 kg/(m²·h) or more is still more preferable.

When the permeation flux of water in the membrane separation step is in the range above, in the case of obtaining a product directly from the membrane separation step, the production efficiency is increased and in the case of returning the alcohol to the adsorption column from the membrane separation step, the energy efficiency of the adsorption column is increased. In addition, in the case where the value of the permeation flux is large, it is also possible to design the system to decrease the separation membrane area with maintaining the desired concentrated amount and concentrating speed in the membrane separation step, and the apparatus can be made compact as well.

The concentration of water in the membrane permeate in the membrane separation step using the membrane separation unit according to the present invention is usually 90% by mass or more; 95% by mass or more is preferable; 99% by mass or more is more preferable; and 99.9% by mass or more is still more preferable. Within this range, the loss amount of alcohol in the membrane separation step decreases, and the production efficiency of high-concentration alcohol increases.

Although the present invention is described in greater detail below by referring to specific embodiments, the present invention is of course not limited only to these specific embodiments.

FIG. 1 is a flow sheet illustrating one example of the production method of an alcohol according to the embodiment of the present invention.

In FIG. 1, a raw material is provided to a rectification column 1 from a raw material tank 10 storing a liquid containing ethanol, such as bioethanol, and water, and a concentrated water-alcohol mixture (for example, an ethanol concentration of 91.0% by mass) is obtained from the top of the rectification column 1.

The top liquid of the rectification column 1 is evaporated in a vaporizer 2 to provide an overheated water-alcohol mixture vapor, and the water-alcohol mixture vapor is provided to an adsorption column 3a. In the adsorption column 3a, water contained in the water-alcohol mixture vapor is adsorbed to obtain high-concentration ethanol (first concentrated alcohol) (for example, an ethanol concentration of 99.5% by mass), which is transported to a product tank 5.

On the other hand, the adsorption column 3b is an adsorption column that has been already used for adsorption of water contained in the water-alcohol mixture vapor, and a lot of water is adsorbed in the inside. Accordingly, while the water-alcohol mixture vapor is provided to the adsorption column 3a to adsorb water contained in the water-alcohol mixture vapor, part of the high-concentration ethanol (first concentrated alcohol) vapor obtained in the adsorption column 3a is provided to the adsorption column 3b to desorb the water adsorbed in the adsorption column 3b and obtain hydrous ethanol (for example, an ethanol concentration of 67.4% by mass).

Conventionally, the hydrous ethanol obtained in the desorption step of thus desorbing water from the adsorption column 3b conventionally had a large water content and could not be directly introduced into a membrane separation unit. Accordingly, the obtained hydrous ethanol was reintroduced into the rectification column located on the upstream side to enable recycling thereof.

In the present process, a specific zeolite membrane composite is used for the membrane separation unit 4, and the hydrous ethanol can thereby be introduced into the membrane separation unit 4 and recycled. According to this embodiment, in the recycling of hydrous ethanol obtained in the water desorption step, a method with high energy efficiency can be employed.

The hydrous ethanol introduced into the membrane separation unit 4 can be obtained as high-concentration ethanol (second concentrated alcohol) (for example, an ethanol concentration of 99.5% by mass) and is provided to a product tank 5.

Figure 2:
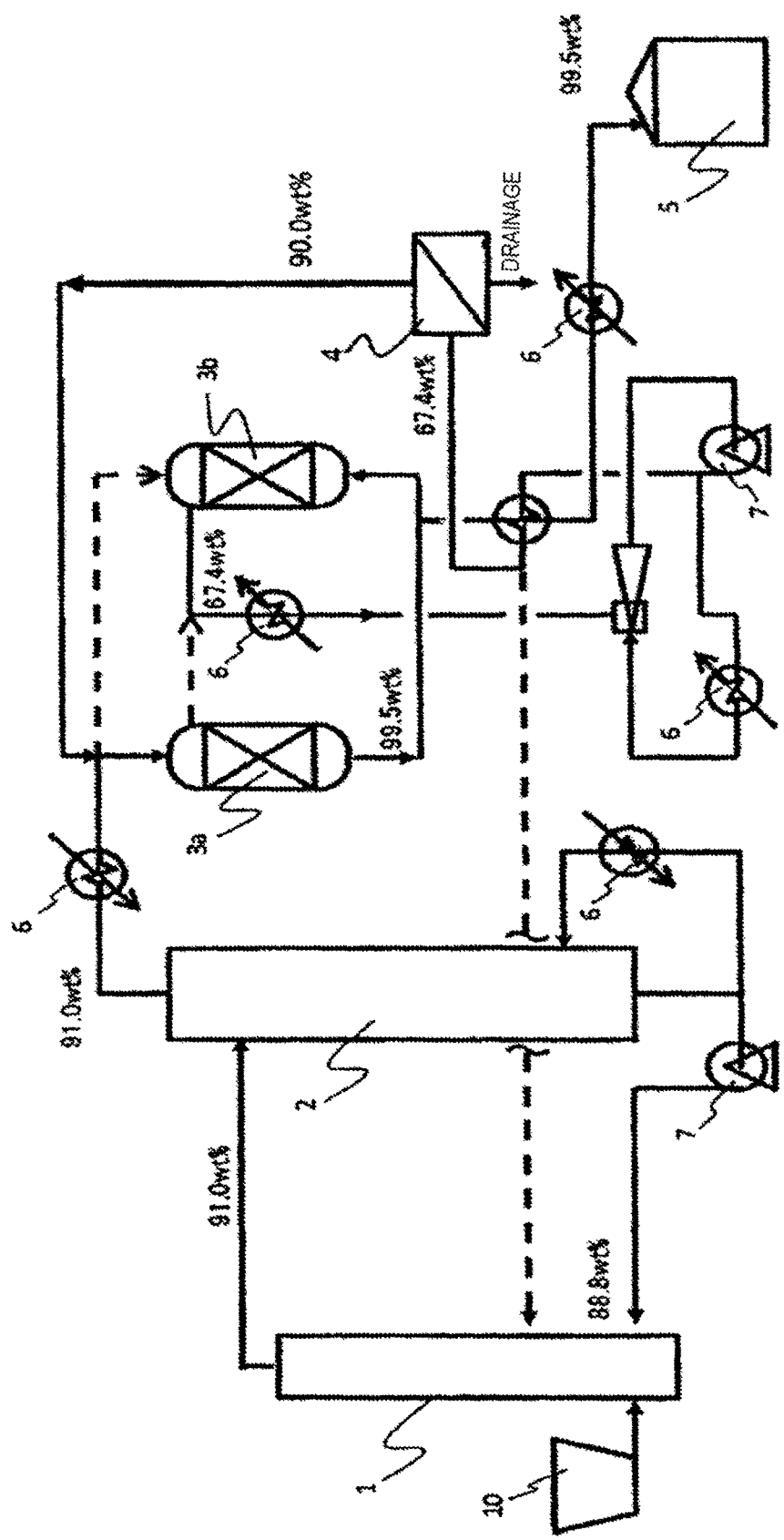
FIG. 2 is a flow diagram illustrating one example of the production method of an alcohol according to the embodiment of the present invention.

FIG. 2 is a flow sheet illustrating another example of the production method of an alcohol according to the embodiment of the present invention.

FIG. 2 is a modified example of the process illustrated in FIG. 1, and, for example, when the ethanol obtained in the membrane separation step is not ethanol having a sufficiently high concentration (for example, an ethanol concentration of 90.0% by mass), the ethanol is re-introduced into the adsorption column 3a to further increase its purity.

This modified example can be employed according to the concentration of the ethanol obtained after the introduction into the membrane separation unit 4 by taking into account, for example, the ethanol concentration of hydrous ethanol provided from the water desorption step in the adsorption column 3b, or the separation capacity of the membrane separation equipment.

Figure 3:
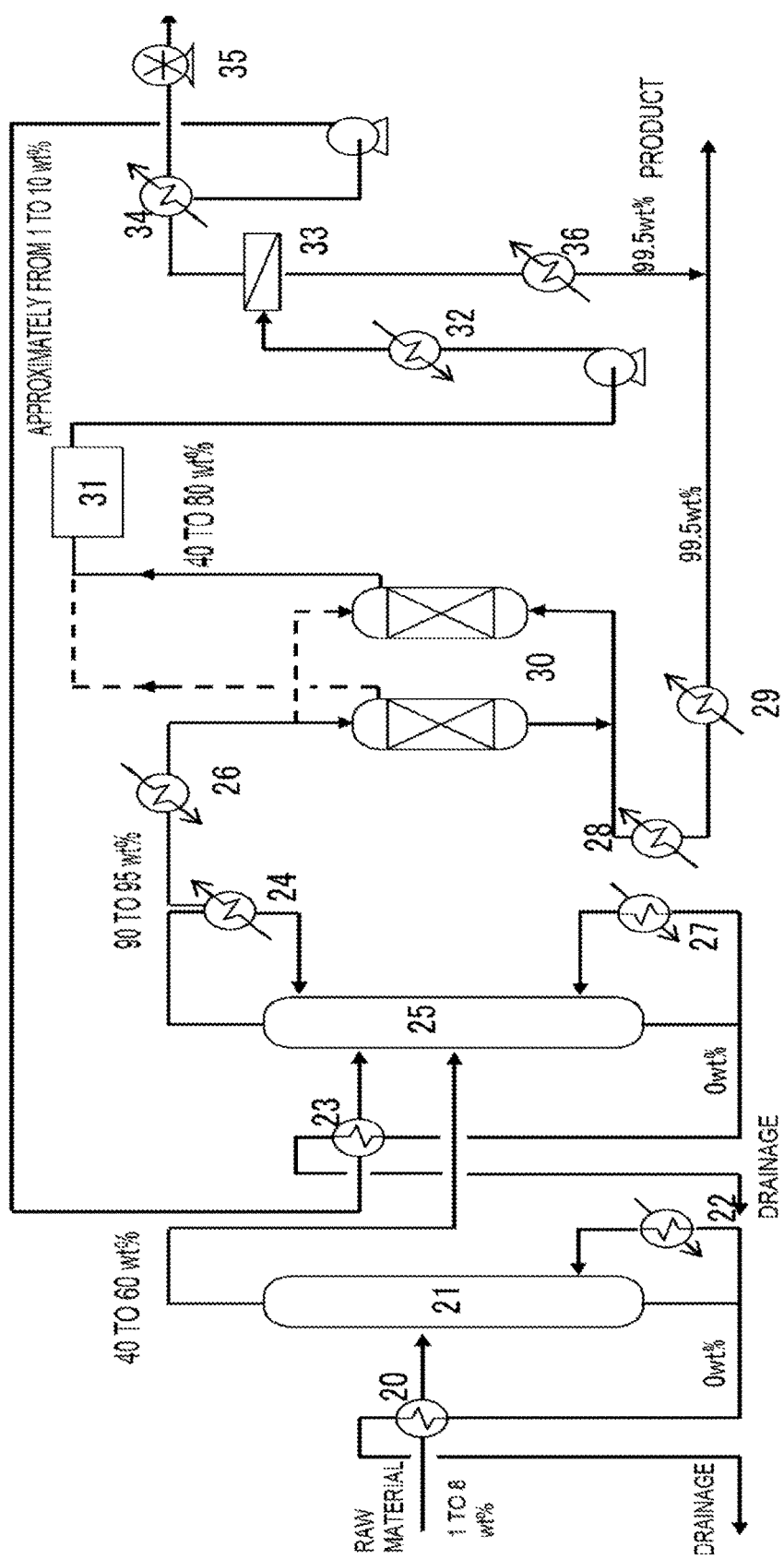
FIG. 3 is a flow diagram illustrating one example of the production method of an alcohol according to the embodiment of the present invention.

FIG. 3 is a flow sheet illustrating one example of the embodiment of the present invention.

A raw material having an alcohol concentration of 1 to 8% by mass is provided to a mash column 21 and preliminarily distilled to obtain a vapor of water-alcohol mixture having an alcohol concentration of 40 to 60% by mass. The water-alcohol mixture vapor is provided to a rectification column 25 to obtain a water-alcohol mixture having an alcohol concentration of 90 to 95% by mass. The obtained water-alcohol mixture vapor is provided to an adsorption column 30 to obtain a first concentrated alcohol and at the same time, a vapor of hydrous alcohol having an alcohol concentration of 40 to 80% by mass is obtained from the adsorption column under regeneration and desorption. This hydrous alcohol vapor turns to liquid in a decompression unit (with a condenser) 31, and the hydrous alcohol in the liquid form is provided to a membrane separation unit 33. In the membrane separation unit 33, water and alcohol are separated by the pervaporation process to obtain a second concentrated alcohol and at the same time, water and alcohol (alcohol concentration: from 1 to 10% by mass) permeated through the membrane are returned to the rectification column 25.

Figure 4:
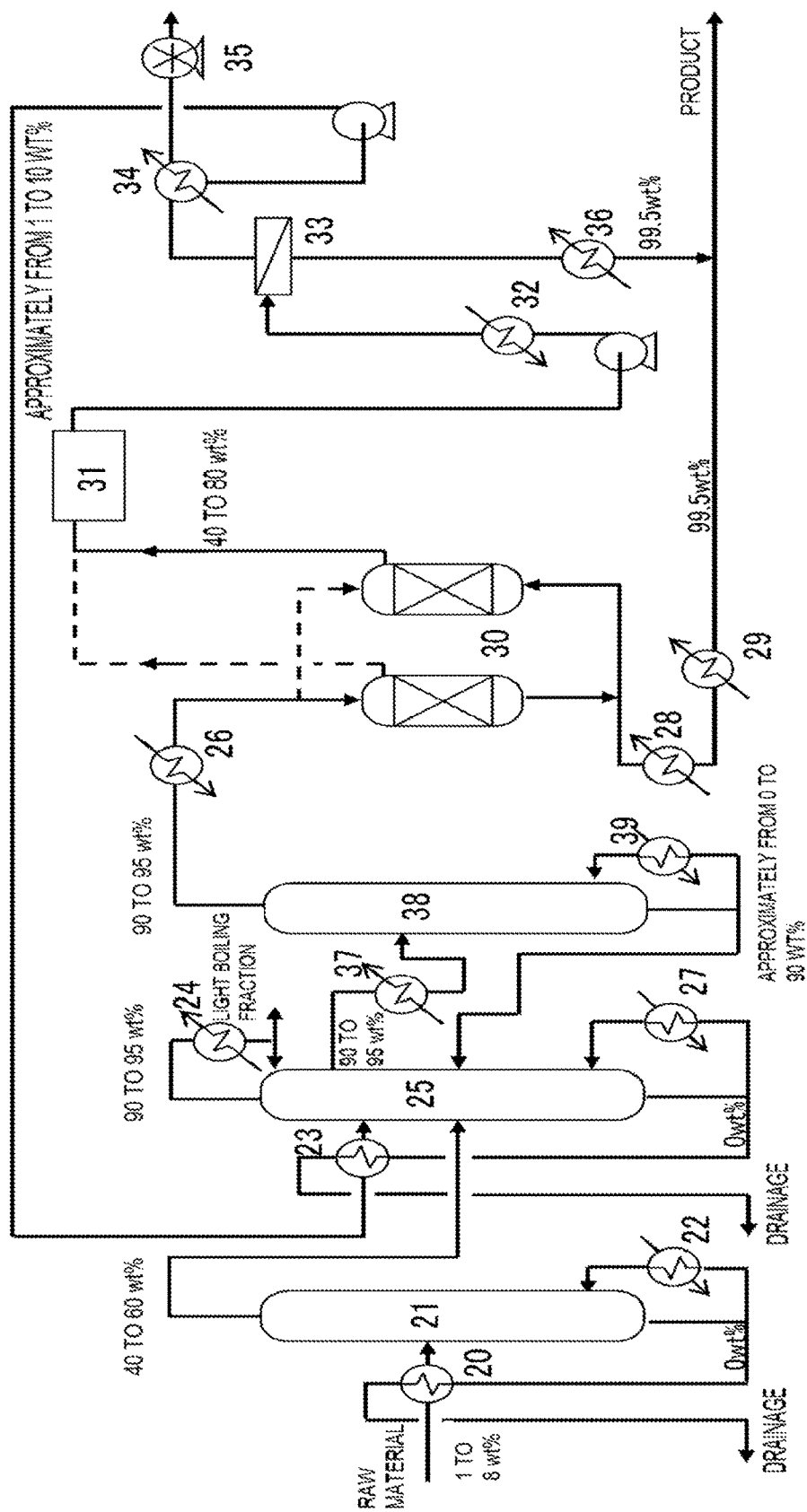
FIG. 4 is a flow diagram illustrating one example of the production method of an alcohol according to the embodiment of the present invention.

FIG. 4 is a flow sheet illustrating one example of the embodiment of the present invention. In contrast with the embodiment of FIG. 3, in this embodiment, a vaporizer 38 is provided as a post-step of the rectification column.

Figure 5:
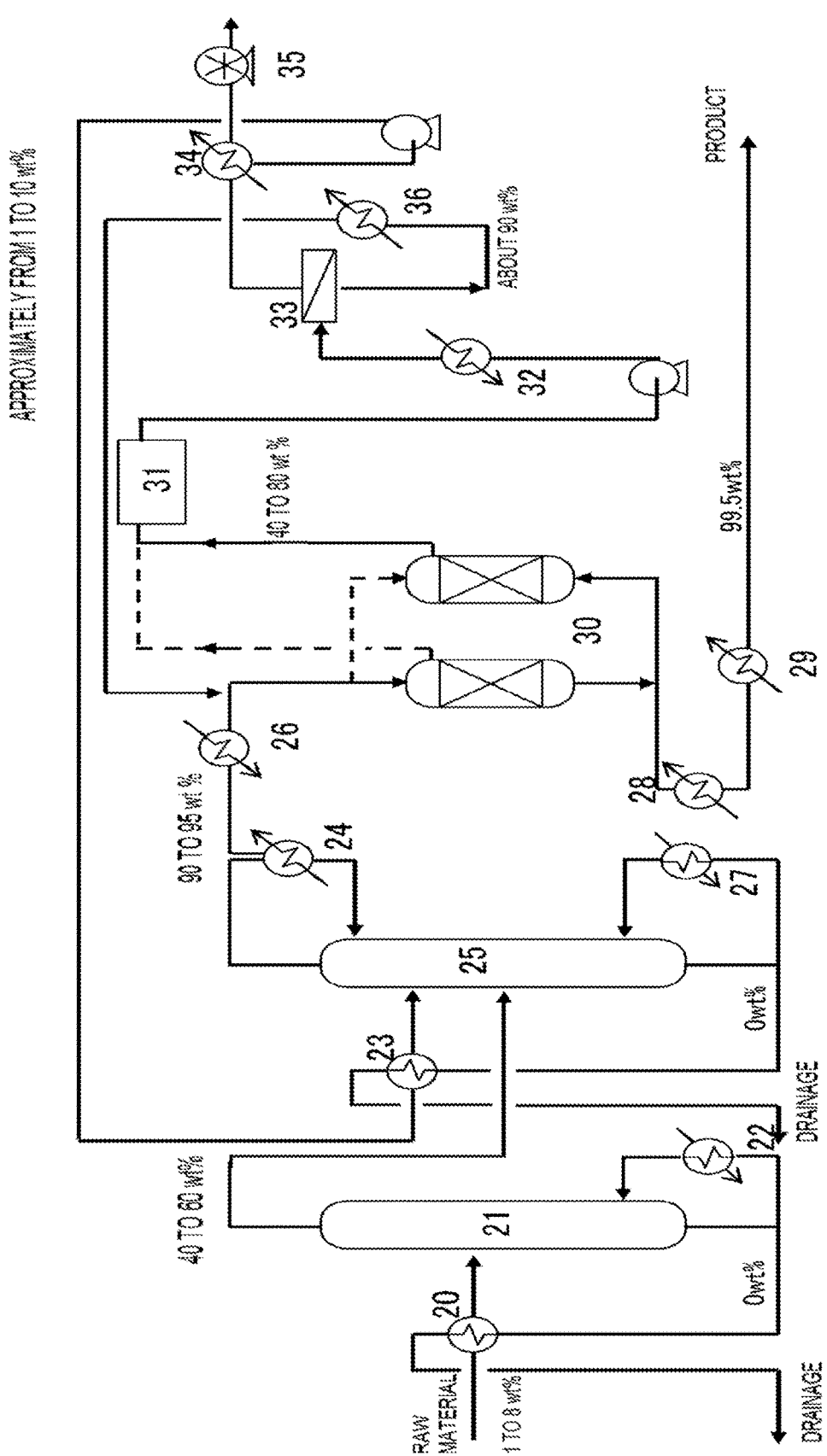
FIG. 5 is a flow diagram illustrating one example of the production method of an alcohol according to the embodiment of the present invention.

FIG. 5 is a flow sheet illustrating one example of the embodiment of the present invention. In contrast with the embodiment of FIG. 3, the second concentrated alcohol obtained in the membrane separation unit is returned to the adsorption column 30.

EXAMPLES

Although the present invention is described more specifically by referring to Examples, the present invention is not limited to the descriptions in the following Examples as long as the gist thereof is observed.

Example 1

The following mixture was prepared as an aqueous reaction mixture for hydrothermal synthesis.

An aqueous 1 mol/L-KOH solution and water were added to aluminum hydroxide (containing 53.5% by mass of $Al_2O_3$, produced by Aldrich), mixed/stirred and thereby dissolved to provide a solution.

Colloidal silica (Snowtex-40, produced by Nissan Chemicals Industries, Ltd.) was added thereto, and the mixture was stirred for 2 hours to prepare an aqueous reaction mixture.

The composition (molar ratio) the aqueous reaction mixture was $SiO_2/Al_2O_3/KOH/H_2O=1/0.125/0.7/80$ and $SiO_2/Al_2O_3=8$.

As the inorganic porous support, a porous alumina tube (outer diameter: 12 mm, inner diameter: 9 mm) was used.

A mixture obtained by mixing 5.00 g of NaOH and 100 g of water with 10.0 g of proton-type Y-type zeolite (HY (SAR=5) produced by Catalysts & Chemicals Ind. Co., Ltd.) was heated at 100° C. for 7 days and then subjected to filtration, water washing and drying to obtain FAU-type zeolite. The particle size distribution of the FAU-type zeolite was measured, as a result, D50 was 1.73 μm and the maximum values were 1.32 μm and 2.98 μm. This FAU-type zeolite was used as the seed crystal.

The support above was dipped in a dispersion obtained by dispersing 0.5% by mass of the seed crystal in water for a predetermined time and then dried at 100° C. for 5 hours or more to attach the seed crystal. The mass of the seed crystal attached was 0.48 $g/m^2$.

The support attached with the seed crystal was dipped in the vertical direction in a Teflon (registered trademark)-made inner cylinder (200 ml) containing the aqueous reaction mixture above and after tightly closing the autoclave, the temperature was raised from room temperature to 180° C. over 5 hours. After the completion of temperature rise, the support was heated at 180° C. for 24 hours in a standstill state under self-generated pressure. After the elapse of a predetermined time, the system was allowed to cool, and the porous support-zeolite membrane composite was taken out of the aqueous reaction mixture, washed and then dried at 100° C. for 4 hours.

The air permeation amount of the porous support-zeolite membrane composite after drying was 4 $L/(m^2 \cdot h)$. The $SiO_2/Al_2O_3$ molar ratio from the membrane surface of the zeolite membrane was measured by SEM-EDX measurement (membrane surface) and found to be 6.

Using the obtained porous support-zeolite membrane composite having a zeolite membrane containing CHA-type zeolite having an $SiO_2/Al_2O_3$ molar ratio of 6, a membrane separation step of selectively allowing permeation of water from hydrous ethanol (water/ethanol=30/70% by mass) as a to-be-separated liquid at 60° C. by the pervaporation process was performed.

Figure 6:
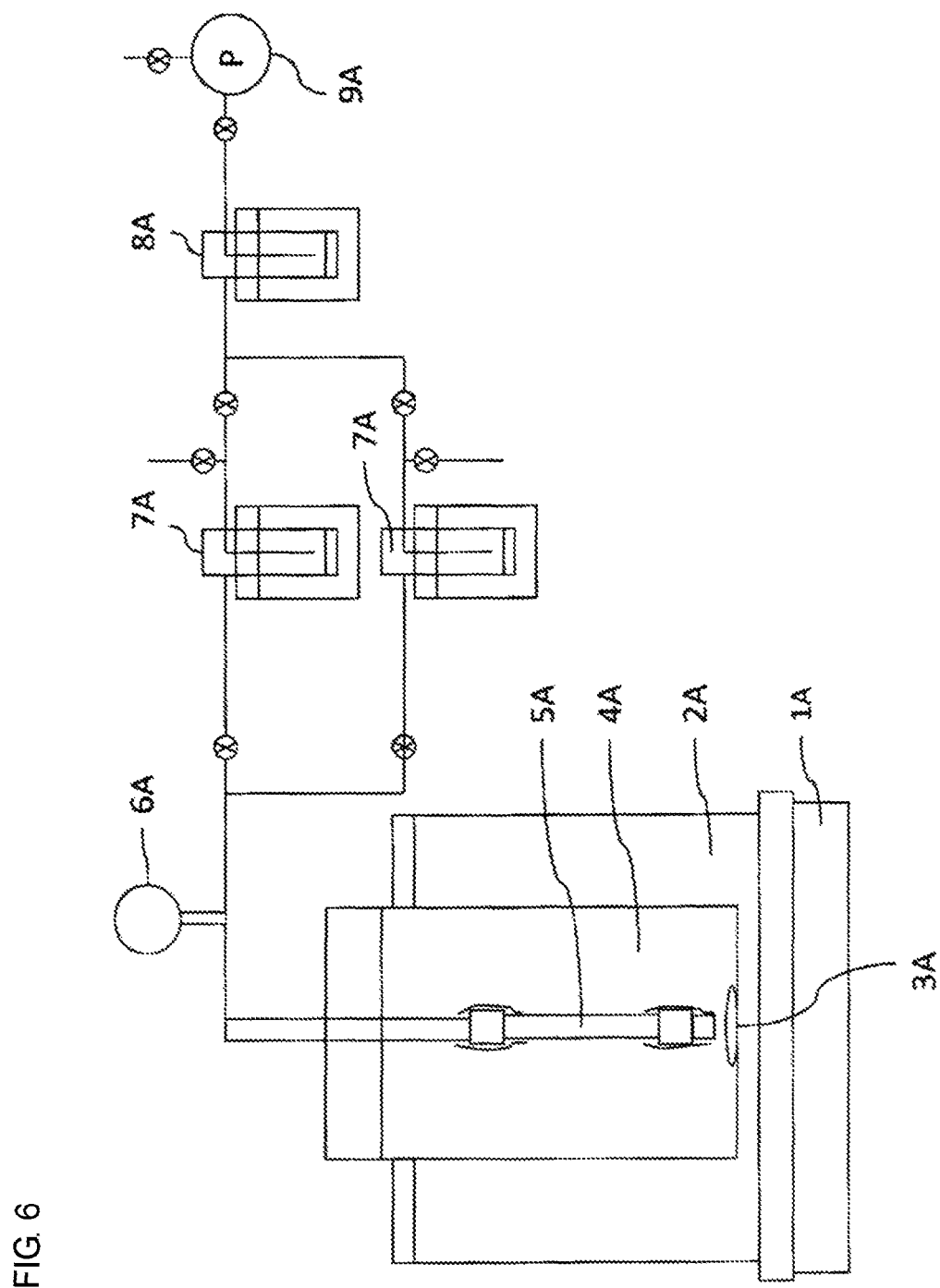
FIG. 6 is a schematic diagram of the apparatus used for the pervaporation process in Examples.

FIG. 6 illustrates a schematic diagram of the apparatus used for the pervaporation process. In FIG. 6, the inside of the porous support-zeolite membrane composite 5A is depressurized by a vacuum pump 9A, and the pressure difference from the outside in contact with the to-be-separated liquid 4A is about 1 atm ($1.01 \times 10^5$ Pa). Owing to this pressure difference, the permeable substance (water) in the to-be-separated liquid 4A pervaporates and permeates through the porous support-zeolite membrane composite 5A. The permeated substance is trapped in a permeated liquid collecting trap 7A. On the other hand, the organic compound in the to-be-separated liquid 4A stays outside the porous support-zeolite membrane composite 5A.

As a result, the permeation flux of the porous support-zeolite membrane composite was 4.4 kg/(m²·h), and the water concentration in the permeated liquid was 99.95% by mass. The water permeance was 4.6×10−6 mol/(m²·s·Pa). The measurement results are shown in Table 1.

Example 2

By using a zeolite membrane composite having a zeolite membrane containing CHA-type zeolite having an $SiO_2/Al_2O_3$ molar ratio of 7, a membrane separation step of selectively allowing permeation of water from hydrous ethanol (water/ethanol=49/51% by mass) as a to-be-separated liquid at 100° C. by the pervaporation process was performed.

Figure 7:
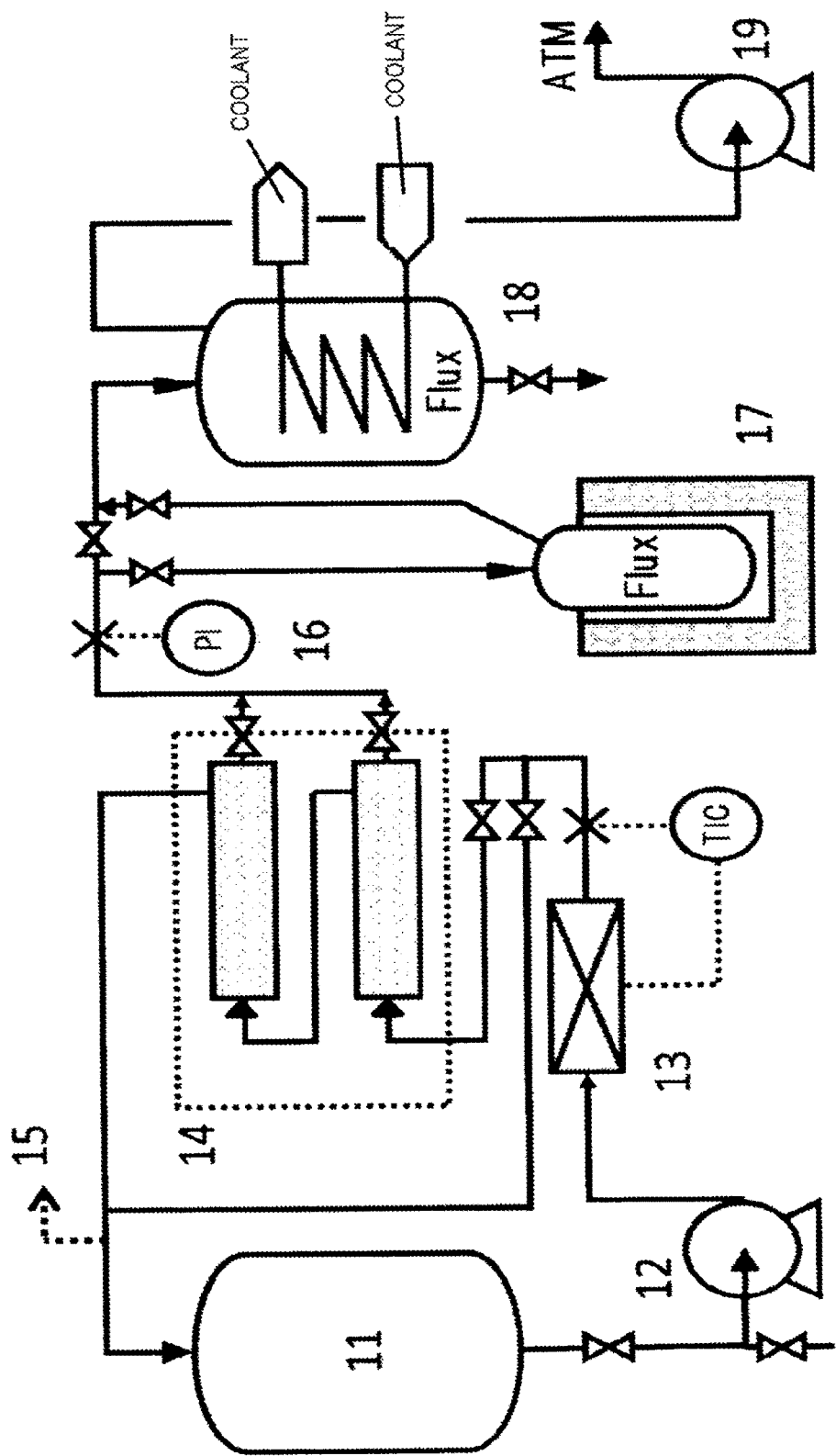
FIG. 7 is a schematic diagram of the apparatus used for the pervaporation process in Examples.

FIG. 7 illustrates a schematic diagram of the apparatus used for the pervaporation.

In FIG. 7, a to-be-separated liquid (volume: 4.0 L) in the raw material tank 11 is provided at a flow rate of 1.0 L/min to a membrane separation unit 14 by a circulating pump 12.

The to-be-separated liquid is heated at 100° C. by an electric heater 13 before introduction into the membrane separation unit 14. The inside of the zeolite membrane composite in the membrane separation unit 14 is depressurized by a vacuum pump 19, and the pressure difference from the outside in contact with the to-be-separated liquid introduced into the membrane separation unit 14 is about 1 atm. Owing to this pressure difference, water working out to the permeable substance in the to-be-separated liquid in the membrane separation unit 14 pervaporates and permeates through the zeolite membrane composite.

The permeated substance is trapped in a cold trap 17. On the other hand, the concentrated ethanol is returned to the raw material tank 11. The concentration of the liquid collected in a sampling line 15 after the elapse of a given time and the weight and concentration of the permeated substance trapped in the cold trap 17 were measured to determine the permeation flux of water.

The composition analyses of the permeated liquid trapped in the cold trap 17 and the to-be-separated liquid were performed by gas chromatography. The permeation flux of water was 12.2 kg/(m²·h), and the water concentration in the permeated liquid was 99.99% by mass. The measurement results are shown in Table 1.

Example 3

A membrane separation step of selectively allowing permeation of water from hydrous ethanol (water/ethanol=32/68% by mass) at 100° C. by the pervaporation process was performed in the same manner as in Example 2. The permeation flux of water was 10.4 kg/(m²·h), and the water concentration in the permeated liquid was 99.99% by mass. The measurement results are shown in Table 1.

Example 4

A membrane separation step of selectively allowing permeation of water from hydrous ethanol (water/ethanol=15/85% by mass) at 100° C. by the pervaporation process was performed in the same manner as in Example 2. The permeation flux of water was 6.8 kg/(m²·h), and the water concentration in the permeated liquid was 99.99% by mass. The measurement results are shown in Table 1.

Example 5

Using a porous support-zeolite membrane composite having a zeolite membrane containing T-type (ERI/OFF) zeolite having an $SiO_2/Al_2O_3$ molar ratio of 6, a membrane separation step of selectively allowing permeation of water from hydrous ethanol (water/ethanol=31/69% by mass) at 100° C. by the pervaporation process was performed. The permeation flux of water was 3.4 kg/(m²·h), and the water concentration in the permeated liquid was 99.99% by mass. The measurement results are shown in Table 1.

Example 6

A membrane separation step of selectively allowing permeation of water from hydrous ethanol (water/ethanol=15/85% by mass) at 100° C. by the pervaporation process was performed in the same manner as in Example 5. The permeation flux of water was 1.9 kg/(m²·h), and the water concentration in the permeated liquid was 99.99% by mass. The measurement results are shown in Table 1.

Example 7

A membrane separation step of selectively allowing permeation of water from hydrous ethanol (water/ethanol=10/90% by mass) at 100° C. by the pervaporation process was performed in the same manner as in Example 5. The permeation flux of water was 1.4 kg/(m²·h), and the water concentration in the permeated liquid was 99.99% by mass. The measurement results are shown in Table 1.

Comparative Example 1

Using a porous support-zeolite membrane composite having a zeolite membrane containing CHA-type zeolite having an $SiO_2/Al_2O_3$ molar ratio of 20, a membrane separation step of selectively allowing permeation of water from hydrous ethanol (water/ethanol=50/50% by mass) at 100° C. by the pervaporation process was performed. The permeation flux of water was 2.2 kg/(m²·h), and the water concentration in the permeated liquid was 99.99% by mass. The measurement results are shown in Table 1.

Comparative Example 2

A membrane separation step of selectively allowing permeation of water from hydrous ethanol (water/ethanol=33/67% by mass) at 100° C. by the pervaporation process was performed in the same manner as in Comparative Example 1. The permeation flux of water was 2.1 kg/(m²·h), and the water concentration in the permeated liquid was 99.99% by mass. The measurement results are shown in Table 1.

Comparative Example 3

A membrane separation step of selectively allowing permeation of water from hydrous ethanol (water/ethanol=15/85% by mass) at 100° C. by the pervaporation process was performed in the same manner as in Comparative Example 1. The permeation flux of water was 1.3 kg/(m²·h), and the water concentration in the permeated liquid was 99.99% by mass. The measurement results are shown in Table 1.

A large permeation flux of water in the membrane separation step means that the capacity per unit area to concentrate, per unit time, ethanol in hydrous ethanol obtained from the water desorption step is high. Accordingly, in the case of obtaining a product directly from the membrane separation step, the production efficiency is increased and in the case of returning the ethanol to the adsorption column from the membrane separation step, the energy efficiency of the adsorption column is increased.

TABLE 1

| | To-Be-Separated Liquid Water/Ethanol (% by mass) | Type of Zeolite | $SiO_2/Al_2O_3$ Molar Ratio | Permeation Flux (kg/m² · h) | Water Concentration in Permeated Liquid (% by mass) |
|---|---|---|---|---|---|
| Example 1 | 30/70 | CHA | 6 | 4.4 | 99.95% |
| Example 2 | 49/51 | CHA | 7 | 12.2 | 99.99% |
| Example 3 | 32/68 | CHA | 7 | 10.4 | 99.99% |
| Example 4 | 15/85 | CHA | 7 | 6.8 | 99.99% |
| Example 5 | 31/69 | T | 6 | 3.4 | 99.99% |
| Example 6 | 15/85 | T | 6 | 1.9 | 99.99% |
| Example 7 | 10/90 | T | 6 | 1.4 | 99.99% |
| Comparative Example 1 | 50/50 | CHA | 20 | 2.2 | 99.99% |
| Comparative Example 2 | 33/67 | CHA | 20 | 2.1 | 99.99% |
| Comparative Example 3 | 15/85 | CHA | 20 | 1.3 | 99.99% |

It is understood from these results that a high-concentration alcohol can be efficiently produced by using a zeolite membrane composite having a zeolite membrane containing zeolite having an $SiO_2/Al_2O_3$ molar ratio of 5 to 15.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2014-221970) filed on Oct. 30, 2014, the contents of which are incorporated herein by way of reference.

DESCRIPTION OF REFERENCE NUMERALS AND SIGNS

1 Rectification column
2 Vaporizer
3a, 3b Adsorption column
4 Membrane separation unit
5 Product tank
6 Heat exchanger
7 Pump
10, 11 Raw material tank
12 Circulating pump
13 Electric heater/temperature controller
14 Membrane separation unit
15 Sampling line
16 Vacuum pressure gauge
17 Cold trap
18 Condenser
19 Vacuum pump
20 Mash column feed preheater
21 Mash column
22 Mash column reboiler
23 Recovered water preheater
24 Rectification column condenser
25 Rectification column
26 Superheater
27 Rectification column reboiler
28 Product condenser
29 Product cooler
30 Adsorption column
31 Decompression unit (with a condenser)
32 Heater
33 Membrane separation unit
34 Permeation-side condenser
35 Vacuum pump
36 Concentrate cooler
37 Concentrate condenser
38 Vaporizer
39 Vaporizer reboiler
1A Stirrer
2A Hot-water bath
3A Stirring bar
4A To-be-separated liquid
5A Porous support-zeolite membrane composite
6A Pirani gage
7A Permeated liquid collecting trap
8A Cold trap
9A Vacuum pump

The invention claimed is:

1. A method of producing a high-concentration alcohol which is methanol or ethanol, with an adsorption column and a membrane separation unit,
the method comprising:
(A) introducing a water-alcohol mixture into the adsorption column to adsorb water on the adsorption column and obtain a first concentrated alcohol,
(B) introducing the first concentrated alcohol obtained in (A) into the adsorption column to desorb the water adsorbed and obtain a hydrous alcohol, and
(C) after (B), introducing the hydrous alcohol into a membrane separation unit provided with a zeolite membrane composite containing zeolite having an $SiO_2/Al_2O_3$ molar ratio of 5 to 15 to obtain a second concentrated alcohol.

2. The method according to claim 1, wherein the zeolite is zeolite having a framework density of 10.0 to 18.0 T/1000 Å.

3. The method according to claim 1, wherein the zeolite is CHA-type zeolite.

4. The method according to claim 1, wherein the water-alcohol mixture is a distillate obtained at the top of a rectification column before (A) and (B).

5. The method according to claim 1, wherein a plurality of adsorption columns are present.

6. The method according to claim 1, wherein the second concentrated alcohol obtained is reintroduced in an adsorption column in (A).

7. The method according to claim 1, wherein the alcohol is ethanol and the water-alcohol mixture is obtained by alcohol fermentation with fermentative bacteria.

8. The method according to claim 1, wherein the water-alcohol mixture further comprises an acid.

9. The method according to claim 1, wherein the-membrane separation is performed by pervaporation.

10. The method according to claim 1, wherein the membrane separation is performed by vapor permeation.

* * * * *